(12) United States Patent
Sorek et al.

(10) Patent No.: US 11,457,804 B1
(45) Date of Patent: Oct. 4, 2022

(54) SYSTEM FOR MONITORING VISION CHANGES

(71) Applicant: AMAZON TECHNOLOGIES, INC., Seattle, WA (US)

(72) Inventors: Noam Sorek, Herzliya (IL); Ilia Vitsnudel, Even Yehuda (IL)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 465 days.

(21) Appl. No.: 16/401,896

(22) Filed: May 2, 2019

(51) Int. Cl.
*A61B 3/032* (2006.01)
*G06F 3/01* (2006.01)
*G06T 7/70* (2017.01)
*G06F 40/109* (2020.01)

(52) U.S. Cl.
CPC ............. *A61B 3/032* (2013.01); *G06F 3/012* (2013.01); *G06F 3/017* (2013.01); *G06F 40/109* (2020.01); *G06T 7/70* (2017.01)

(58) Field of Classification Search
None
See application file for complete search history.

(56) References Cited

U.S. PATENT DOCUMENTS

| | | | |
|---|---|---|---|
| 2011/0279458 A1* | 11/2011 | Gnanasambandam | ..................... G06Q 30/0251 358/1.15 |
| 2016/0286204 A1* | 9/2016 | Grata | ........................ G02F 1/33 |
| 2017/0177166 A1* | 6/2017 | Kockan | ................ A61B 3/0025 |
| 2017/0181848 A1* | 6/2017 | Hyde | .................... A61F 2/1627 |
| 2019/0187870 A1* | 6/2019 | Bostick | ............... G06F 3/04886 |
| 2020/0202121 A1* | 6/2020 | Konin | .................. G06F 3/0219 |

* cited by examiner

*Primary Examiner* — Talha M Nawaz
(74) *Attorney, Agent, or Firm* — Lindauer Law, PLLC

(57) ABSTRACT

Information about changes in vision over time is useful to determine the health of a user. An electronic device has a display that presents visual information to a user. A sensor generates distance data that is used to determine a distance between the user and the display at particular times. Other data may also be acquired that is indicative of whether the user is wearing glasses, tilt of the user's head relative to the display, ambient light level, display brightness, what is being presented on the display such as video content or text content, font size, and so forth. The data is used to determine if the user's vision has changed beyond a threshold amount. If so, an action may be taken, such as providing a recommendation to the user. For example, the user may be advised to consult a health care provider.

20 Claims, 7 Drawing Sheets

SYSTEM FOR MONITORING VISION CHANGES

BACKGROUND

Human vision relies on the eyes, optic nerve, and brain to generate and process crucial sensory information. Changes in human vision may be indicative of various health issues.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
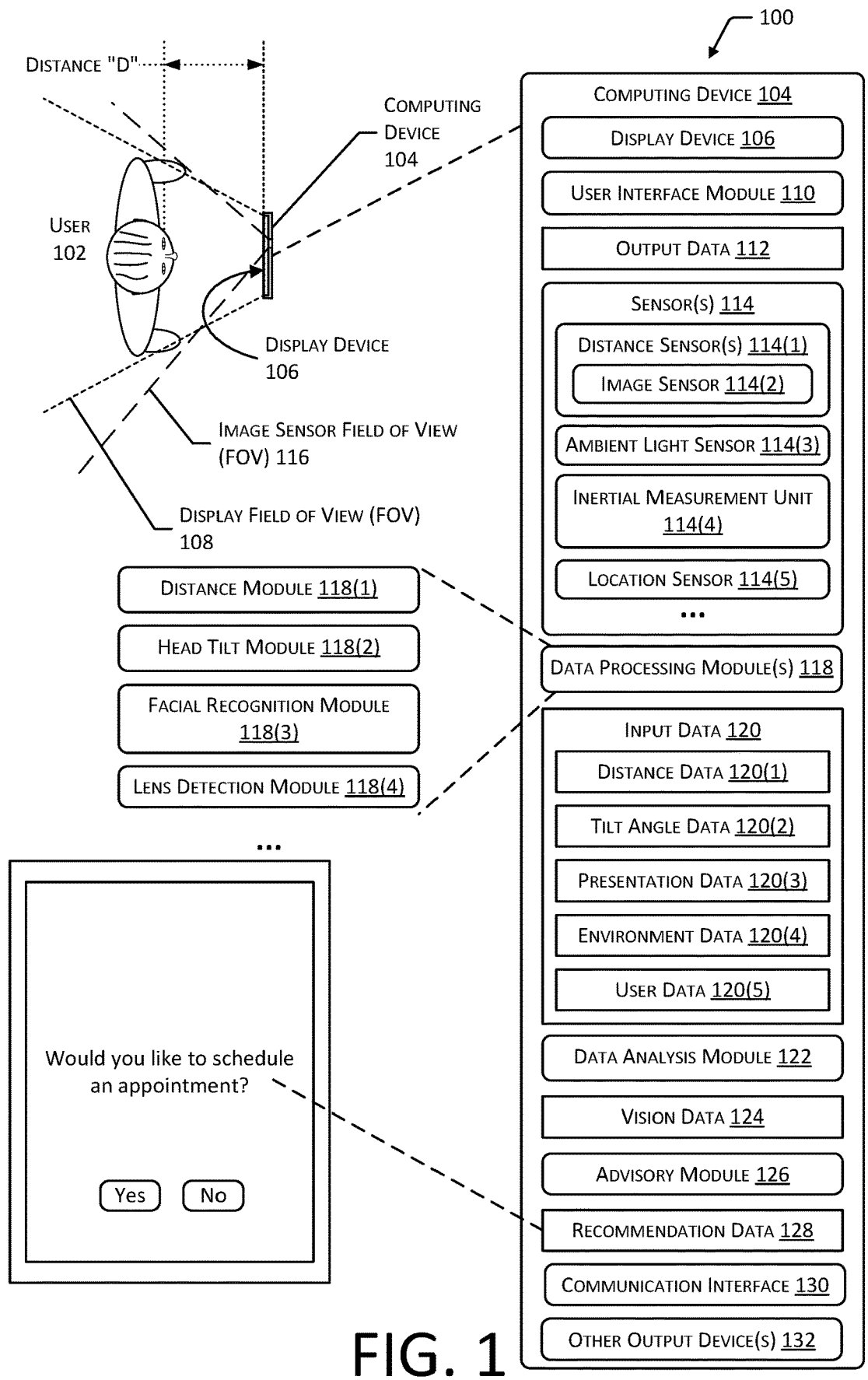
FIG. 1 is an illustrative system that detects vision changes by analyzing data acquired over time that includes the distance between the user and a display screen, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to.

DETAILED DESCRIPTION

Maintaining and improving the wellbeing of a user is facilitated by detecting changes in their health. Human vision is complex and involves many organs including eyes, optic nerve, and brain. Because of the interrelationships between the various organ systems in the body, performance of the human vision system may be affected by changes in any of these or other organs. For example, visual acuity may degrade with age due to reduced ability to change the shape of the lens in the eye or clouding of the lens. In another example, prolonged periods of increased blood glucose levels resulting from uncontrolled diabetes may produce diabetic retinopathy leading to blindness.

Some changes in vision may occur suddenly. For example, such as loss of vision, flashing lights, "floaters", a gray curtain moving across the field of vision, and so forth. While serious, the rapid onset may be readily observed by the user or by a caregiver who observes unusual behavior. However, other changes to vision are more gradual.

Gradual vision changes can be insidious and difficult for the user to recognize. Humans have significant ability to compensate and may do so without being consciously aware of the compensation. For example, as the eye loses the ability to focus the user may adjust the distance between their eye and something they are looking at, such as a tablet computer, to bring the image on a display device of the tablet into better focus.

Access to regular health care is an important part of maintaining wellbeing. However, significant changes may occur between visits with a health care provider. In some situations a user may have limited or no access to a health care provider. As a result, the changes may not be recognized by the user or detected by someone else. Early detection of a change in health can lead to earlier interventions which may reduce damage, improve wellbeing, reduce treatment costs, and so forth.

Described in this disclosure are devices and techniques to gather input data that is then used to detect vision changes in a user. A user may opt in to allow gathering input data over extended periods of time, such as days, weeks, months, and so forth. The input data may include a timestamp indicating when data was obtained, distance data that indicates a distance between a display device and the user, tilt angle data that indicates a relative angle between the display device and the user, and so forth.

The distance data may be obtained using a distance sensor such as a time-of-flight, camera, ultrasound, and so forth. As the user's vision changes, the distance between the head of the user and the display device may change. For example, if the user is losing visual acuity due to retinal disease, they may try to keep the image on the display device in focus by reducing the distance between their eyes and the display device. In another example, if the user is suffering from presbyopia they may move to increase the distance between their eyes and the display device.

The tilt angle data may be determined using various sensors including, but not limited to the distance sensors. In one implementation, a camera may be mounted near the display device. During operation of the display device, an image of the user is acquired. The image may be processed to determine a tilt angle of the user's head relative to the camera. Given a known relationship between the display device and the location of the camera, the tilt angle between the user's head and the display device may be determined.

The tilt angle is useful in determining changes in vision due to the use of multi-focal lenses. A user may be wearing glasses with multi-focal lenses while viewing the display device. A multi-focal lens has different refractive characteristics at different regions on the lens. For example, a bifocal lens may have a first region with a +0.25 diopter for general use and a second region with a +2 diopter for closer viewing. The user wearing multi-focal lenses tilts their head relative to what they are trying to view to bring a desired region of the lens into their central vision. Alternatively, if the display device is moveable, the user may move the display device into view through the desired region. Continuing the example, while looking at the display device of the tablet, the user may tilt their head relative to the display device.

This tilt places the second region with the +2 diopter refraction into the line of central vision, bringing the view of the display device into comfortable focus.

Other input data may also be acquired and used to determine vision changes. Presentation data may include information about the image presented by the display device. For example, presentation data may include font size, font color, background color, display brightness level of the display device, display resolution, display physical size, type of content, and so forth. Environment data may include information about ambient light level, motion, location, and so forth. User data may include information such as a user identifier, whether lenses are detected on the user, pupil width, and so forth.

The input data is processed to determine vision data. The vision data may include a visual acuity metric that is based on one or more of distance, tilt angle, font size, display brightness, and so forth. The vision data may include a dilation metric that is based on pupil dilation. A change in the visual acuity metric from a first time to a second time that exceeds a threshold value may be representative of a change in vision.

In some implementations, the system may attempt to mitigate effects of the vision change. For example, if the visual acuity has decreased, the font size may be increased, font color and background color may be set to increase contrast, and so forth.

The vision data may be used to determine recommendation data. For example, the user may have been holding the tablet so that the display device is closer and closer to their eyes over the past several weeks. The vision data indicates this with a decreasing visual acuity metric over that period of time. The decrease exceeds a threshold value, and the system generates recommendation data. For example, the recommendation data may ask the user if they have been having trouble reading. If the user responds yes, the system may facilitate communication with the user's health care provider to arrange an eye examination.

The system may also operate in conjunction with data from other devices. For example, the user may have a wearable device that provides information about movement, cardiac pulse, blood pressure, and so forth. This information may be used in conjunction with the input data or the vision data to provide additional information to the user to assist in their well-being. For example, if the vision data indicates a degradation in visual acuity and an increase in blood pressure occurs over the same period, recommendation data may be provided that suggests consulting a health care provider. Continuing the example, the change in visual acuity may be less than the threshold level, but in conjunction with the change in blood pressure may result in a recommendation being provided.

By using the devices and techniques described in this disclosure, information is provided to a user to more quickly and effectively detect changes in vision. This information may be used to provide recommendations to improve the wellbeing of the user and may also, when possible, aid in mitigating the effects of those changes.

Illustrative System

FIG. 1 is an illustrative system 100 that detects vision changes by analyzing input data that has been acquired over time. A user 102 in an environment may interact with a computing device 104. The computing device 104 may use a display device 106 to present information visually to the user 102. The display device 106 may be used to present content that includes text, images, and so forth. For example, the display device 106 may be used to present a webpage that includes text, still images, video, animation, and so forth. The display device 106 is visible within a display field of view (FOV) 108. In this illustration the display device 106 is incorporated into the computing device 104. For example, the computing device 104 may comprise a tablet computer or smartphone that includes the display device 106. In other implementations, the display device 106 may be separate from the computing device 104. The computing device 104 and the display device 106 may be part of a vehicle, internet connected device, home automation device, desktop computer, laptop computer, television, and so forth.

The computing device 104 includes, or is in communication with, other devices. A user interface module 110 generates output data 112 for presentation using one or more output devices. For example, the user interface module 110 may comprise a rendering engine that processes hypertext markup language (HTML) to generate output data 112 comprising an image of a graphical user interface. The image may then be presented on the display device 106. The user interface module 110 may be used to obtain input from the user 102. For example, the display device 106 may include a touch sensor. The user 102 may touch areas on the display device 106 that are associated with particular controls. Data from the touch sensor that is indicative of these touches may be processed by the user interface module 110 to determine input of the user. In other implementations other types of output data 112 may be presented. For example, output data 112 representative of sound may be presented using speakers.

The computing device 104 includes, or is in communication with, other devices. These devices include one or more sensors 114 that generate sensor data. The sensors 114 may include one or more of: one or more distance sensors 114(1) which may include an image sensor 114(2), an ambient light sensor 114(3), an inertial measurement unit (IMU) 114(4), a location sensor 114(5), and so forth.

The distance sensors 114(1) provide information indicative of a distance between an object, such as the user 102 or a portion thereof, and the distance sensor 114(1). The image sensor 114(2) may comprise a "forward facing" camera with an image sensor field of view (FOV) 116 that is coincident with at least a portion of the display FOV 108. For example, the image sensor 114(2) may be used to obtain an image of the user's 102 head or a portion thereof, while the user 102 is within the display FOV 108.

The ambient light sensor 114(3) provides information about the level of illumination in the ambient environment. The IMU 114(4) may comprise one or more accelerometers, gyroscopes, tilt sensors, and so forth. The IMU 114(4) may provide information indicative of movement. The location sensor 114(5) provides information about a relative or absolute location. For example, a relative location may be "kitchen" while an absolute location may be indicated by a street address or specific geographic coordinates and altitude. The sensors 114 are discussed in more detail below with regard to FIG. 2.

One or more data processing modules 118 generate input data 120 during operation of the computing device 104, such as after the user 102 allows information to be acquired. For example, the user interface module 110 may present a user interface on the display device 106 that informs the user 102 how the input data 120 will be acquired and used. Continuing the example, if the user 102 opts in, the system may operate as described.

The data processing modules 118 may include one or more of a distance module 118(1), head tilt module 118(2), lens detection module 118(4), facial recognition module 118(3). The input data 120 may include an index such as a timestamp, sequence number, and so forth. For example, a timestamp may be used to associate data with a particular time or window of time.

The distance module 118(1) determines distance data 120(1) that is indicative of a distance "D" between the display device 106 and the user 102. For example, the distance data 120(1) may be indicative of a distance to the eyes, face, or other portion of the user's 102 head. In one implementation, the distance sensors 114(1) may include an optical time of flight (TOF) sensor located near the display device 106. The TOF sensor may generate sensor data indicative of a distance to an object, such as the head of the user 102. The sensor data may be processed to determine the distance data 120(1). For example, the sensor data may comprise 90 samples that are averaged to generate the distance data 120(1). In another implementation, the distance sensors 114(1) may include an image sensor 114(2) that acquires an image of the user 102. The image is processed to determine the presence of various features. For example, the image of the user's face may be processed to determine the location of two or more features within the image, such as the pupils. Based on a distance between the locations in the image of the two or more features, the distance data 120(1) may be determined. The distance data 120(1) may be expressed in terms of linear units such as meters, in terms of time such as in microseconds, as pixels, as a dimensionless number, and so forth.

The head tilt module 118(2) determines tilt angle data 120(2) that is indicative of a relative angle between the display device 106 and the head of the user 102. For example, the tilt angle may be an angle between a first line extending from (and orthogonal to) a plane of the display device 106 and a second line formed by an intersection of the coronal plane and the sagittal plane of the head.

In one implementation, the head tilt module 118(2) may use one or more of the distance sensors 114(1) to determine the distance to two or more parts of the head of the user 102. For example, a range camera may be used to acquire an image of the head that includes distance measurements associated with a plurality of points within the image, such as a distance for each pixel within the image. The image may be processed to determine two or more portions, such as the forehead and the chin of the user 102. The distance to each of the portions may be used to determine the tilt angle data 120(2). For example, if a first distance to the forehead is within a threshold percentage of a second distance to the chin, the tilt angle may be determined to be 90 degrees.

In another implementation, the head tilt module 118(2) may use an image of the user 102 that is acquired by an image sensor 114(2). The image is then processed to determine a pose of the head with respect to the camera. For example, the image of the user's head may be processed by a neural network that has been trained to provide a tilt angle output based on image input.

The data processing modules 118 may determine presentation data 120(3). The presentation data 120(3) is indicative of the information that is being presented by the display device 106. For example, the presentation data 120(3) may comprise information indicative of font size, font color, background color, display resolution, display physical size, type of content, and so forth. The presentation data 120(3) is discussed in more detail with regard to FIG. 5.

The data processing modules 118 may determine environment data 120(4). The environment data 120(4) is indicative of the environment of the display device 106. For example, the environment data 120(4) may comprise information indicative of an ambient light level, motion of the computing device 104, location of the computing device 104, and so forth.

The data processing modules 118 may determine user data 120(5). For example, the user data 120(5) may comprise information indicative of a user identifier, that the user 102 is currently wearing lenses such as eyeglasses or contacts, and so forth. A facial recognition module 118(3) may determine one or more features in the image acquired by the image sensor 114(2) and use those features to associate a user identifier with the user 102 in the image. For example, the facial recognition module 118(3) may use a neural network to process an image of the user 102 to determine the user identifier.

In some implementations the facial recognition module 118(3) or another module may generate data indicative of facial expressions. For example, a neural network may be used to determine a facial expression of the user 102 based on image data from the image sensor 114(2). The facial expressions determined may include, but are not limited to, squinting, smiling, frowning, pained, and so forth. The user data 120(5) may include information indicative of the facial expression of the user 102.

A lens detection module 118(4) may determine whether the user 102 depicted in the image acquired by the image sensor 114(2) is wearing lenses. For example, an image of at least a portion of the user's 102 head may be acquired. The lens detection module 118(4) may process the image using a neural network to determine that the user is wearing one or more of glasses, contact lenses, intraocular lenses, and so forth.

In some implementations various functions associated with different modules may be combined. For example, a neural network may be trained to provide output that is indicative of a user identifier and also to provide information as to whether the user 102 is wearing lenses such as eyeglasses. The user data 120(5) is discussed in more detail with regard to FIG. 5.

A data analysis module 122 processes at least a portion of the input data 120 to determine vision data 124. The vision data 124 may comprise information that is indicative of the user's 102 vision at different times. The vision data 124 may be indicative of visual acuity, visual field, color perception, and so forth. In one implementation, the vision data 124 may include a visual acuity metric that is indicative of visual acuity. For example, the visual acuity metric may be based on the font, font size, distance data, and so forth during a particular viewing session. The vision data 124 is discussed in more detail with regard to FIG. 5.

An advisory module 126 may process the vision data 124 to determine recommendation data 128. The recommendation data 128 may then be presented by a user interface. In one implementation the advisory module 126 may analyze the vision data 124 that is associated with a plurality of different times. The advisory module 126 may determine if there are trends associated with a change in vision data 124. For example, the advisory module 126 may perform a statistical analysis on the vision data 124, discarding outliers in the vision data 124 and establishing a trend line. Recommendation data 128 may be generated responsive to the advisory module 126 determining a trend line with a negative slope that exceeds a threshold value. In another implementation the input data 120, the vision data 124, or a combination thereof may be processed by a neural network that provides as output the recommendation data 128. The recommendation data 128 may comprise data such as a recommendation to the user 102 that they should consult with a health care provider.

The computing device 104 may include a communication interface 130. The communication interface 130 may provide communications with other computing devices 104, networks, and so forth. In some implementations the system 100 may facilitate communication between the user 102 and another party, such as a health care provider. For example, the recommendation data 128 may include a prompt asking the user 102 if they would like to schedule an appointment, such as an eye examination with a health care provider. If the user 102 provides input indicative of a "yes", the system 100 may use the communication interface 130 to notify the health care provider.

In some implementations the system 100 may send recommendation data 128 or vision data 124 to another system or user 102. For example, if the computing device 104 is owned by a parent and used by a child, the parent may receive the recommendation data 128 associated with the child's use. In another example, the user 102 may authorize one or more of the vision data 124, the recommendation data 128, or other information from the system 100 to be sent to a health care provider for assessment.

Instead of, or in addition to, the display device 106, the computing device 104 may include other output devices 132. For example, the computing device 104 may use audio output devices such as speakers to provide audible output. In some implementations the system 100 may be used to determine changes in other senses of the user 102. For example, the input data 120 may include information indicative of volume level of the speakers, background noise level in the ambient environment, and so forth. The system 100 may determine changes, such as the user 102 increasing the volume level over time in an otherwise quiet environment while the user 102 is at a consistent distance from the speakers, which may be indicative of hearing loss.

In some implementations, the system 100 may attempt to mitigate effects of the vision change. For example, if the user 102 has been moving closer to the display device 106, the user interface module 110 may be commanded to increase the default font size presented on the display device.

The system 100 may also operate in conjunction with data from other devices. For example, the user 102 may have a wearable device that provides information about movement, cardiac pulse, blood pressure, and so forth. This information may be used in conjunction with the input data 120 or the vision data 124 to provide additional information to the user 102 or care provider. For example, if the vision data 124 indicates a degradation in visual acuity and an increase in blood pressure over the same period, the recommendation data 128 may be provided that suggests consulting a health care provider. Continuing this example, the change in visual acuity may be less than the threshold level that would alone be indicative of a vision change, but in conjunction with the change in blood pressure may result in generation of recommendation data 128.

By using these devices and techniques, changes in vision of the user 102 may be detected more quickly and effectively. This information may be used to mitigate the effects of those changes by changing presentation of information to the user. The information may also be used to improve the wellbeing of the user 102 by recognizing and drawing the attention of the user or a care provider to the change.

Figure 2:
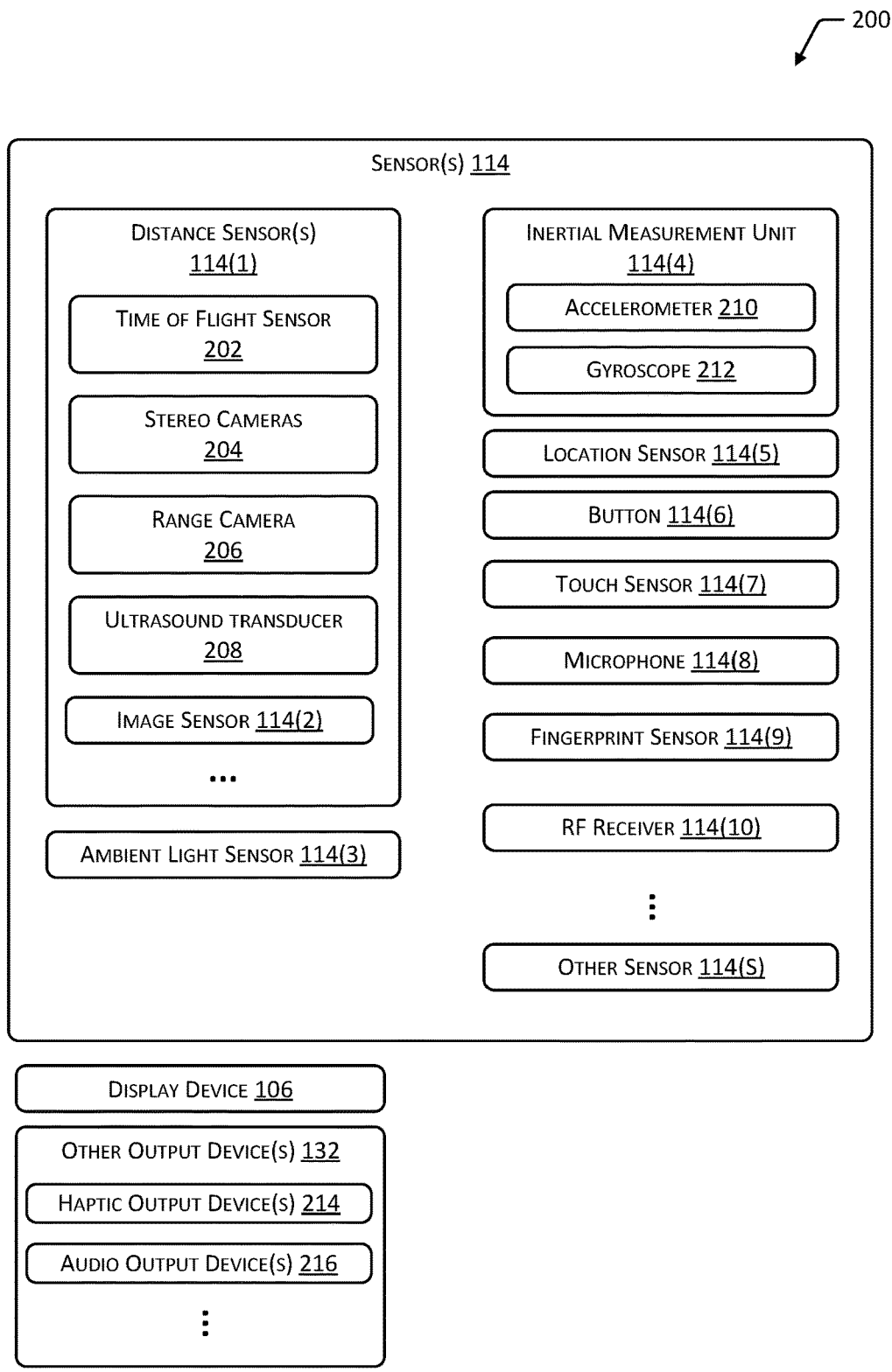
FIG. 2 illustrates a block diagram of sensors and output devices that may be used during operation of the system, according to one implementation.

FIG. 2 illustrates block diagrams of sensors 114 and output devices that may be used during operation of the system 100, according to one implementation.

The sensors 114 may include one or more distance sensors 114(1). The distance sensors 114(1) provide information indicative of a distance between an object, such as the user 102 or a portion thereof, and the distance sensor 114(1). This information is then used to determine the distance data 120(1). For example, if the distance sensor 114(1) is mounted next to the display device 106, the distance data 120(1) may comprise the distance output produced by the distance sensor 114(1). In another example, if the distance sensor 114(1) is located somewhere other than near the display device 106, a correction factor or adjustment may be applied. For example, if the computing device 104 comprises a laptop computer with a display device 106 in an upper portion and a distance sensor 114(1) located in a lower portion, such as between the keyboard and the user, a correction factor may be used to account for the displacement between the distance sensor 114(1) and the display device 106.

The distance sensors 114(1) may include, but are not limited to, an image sensor 114(2), time of flight (ToF) sensors 202, stereo cameras 204, range cameras 206, ultrasound transducers 208, and so forth.

The ToF sensor 202 may use time-of-flight (ToF) to determine a distance from the sensor to an object. For example, ToF determines a propagation time (or "round-trip" time) of a pulse of emitted light from an optical emitter or illuminator that is reflected or otherwise returned to an optical detector. By dividing the propagation time in half and multiplying the result by the speed of light in air, the distance to an object may be determined.

The stereo cameras 204 may comprise an array of two or more cameras separated from one another by a known offset distance. An image is acquired from each camera, and these images compared to determine a disparity between the two images. For example, the relative location of the head of the user 102 in each image will differ due to the offset distance. The difference in the relative locations may then be used to determine a distance from the stereo cameras 204.

The range camera 206 may comprise a camera that acquires an image of a scene as well as distance information to points within the scene. For example, each pixel in an image from a range camera 206 may be associated with a distance between the range camera 206 and the portion of the object that the pixel represents. The range camera 206 may use various techniques including structured light, coded aperture, time of flight, and so forth. For example, a structured light pattern with known features may be provided by the optical emitter. A portion of the structured light pattern may then be detected on the object using an image sensor 114(2). Based on an apparent distance between the known features of the structured light pattern, the distance to the object may be calculated. In another example, a range camera 206 using a coded aperture may determine distance based on apparent blurring of an image obtained through specially constructed apertures.

The ultrasound transducer 208 may comprise one or more transducers. For example, a first transducer may emit an ultrasonic sound while a second transducer detects a reflection of the ultrasonic sound that was emitted. The ultrasound transducer 208 may operate as a sonar device, using the time of flight of the ultrasonic sound to determine a distance to an object.

In other implementations the distance sensor 114(1) may comprise other devices or use other techniques to determine a distance to an object.

The sensors 114 may include an image sensor 114(2). The image sensor 114(2) generates sensor data indicative of one or more images. The image sensor 114(2) may be configured to detect light in one or more wavelengths including, but not limited to, terahertz, infrared, visible, ultraviolet, and so forth. For example, an infrared image sensor 114(2) may be sensitive to wavelengths between approximately 700 nanometers and 1 millimeter. The image sensor 114(2) may comprise charge coupled devices (CCD), complementary metal oxide semiconductor (CMOS) devices, microbolometers, and so forth. The system 100 may include one or more image sensors 114(2). For example, an image sensor 114(2) may be mounted proximate to the display device 106 and have an image sensor FOV 116 that includes at least a portion of the display FOV 108. The image sensor 114(2) may be used to acquire one or more images of the user 102 while they are in the display FOV 108.

One or more of the images produced by the image sensor 114(2) may be processed by the data processing module 118. In one implementation, the distance module 118(1) may process the images from one or more image sensors 114(2) to determine a distance to the user 102. For example, the image from a single image sensor 114(2) is processed to determine the presence of various features, such as the location of the pupils of the user 102. Based on a distance between the locations in the image of the two or more features, the distance data 120(1) may be determined. For example, the distance data 120(1) may be expressed as "241 pixels" indicative of the distance between the features or may be converted into a linear measurement such as "27 cm".

The ambient light sensor 114(3) provides sensor data indicative of ambient lighting conditions such as a level of illumination. The ambient light sensor 114(3) may be sensitive to wavelengths including, but not limited to, infrared, visible, or ultraviolet light. In contrast to the image sensor 114(2), the ambient light sensor 114(3) may typically provide a sequence of amplitude (magnitude) samples and color data while the image sensor 114(2) provides a sequence of two-dimensional frames of samples (pixels). In some implementations the image sensor 114(2) may be used to provide information about the ambient lighting conditions.

The IMU 114(4) may include one or more accelerometers 210, gyroscopes 212, tilt meters, and so forth. The IMU 114(4) provides sensor data indicative of movement of a structure the IMU 114(4) is attached to, such as a frame of the computing device 104 to which the display device 106 is affixed. For example, the sensor data may indicate if the user 102 has the display device 106 tilted with respect to vertical, is moving the display device 106, whether the user's 102 hand is shaking, and so forth. The accelerometer 210 provides accelerometer data indicative of a direction and magnitude of an imposed acceleration. Data such as rate of change, determination of changes in direction, speed, and so forth may be determined using the accelerometer 210. The gyroscope 212 provides rotation data indicative of rotation. The accelerometers 210 and the gyroscopes 212 may comprise mechanical, optical, micro-electromechanical, or other devices. For example, the accelerometer 210 and the gyroscope 212 in may comprise a prepackaged solid-state inertial measurement unit (IMU) with sensors oriented along multiple axes and that provides sensor data along multiple axes.

The location sensor 114(5) provides information about a relative or absolute location. The location sensor 114(5) may comprise an optical, radio, or other navigational system such as a global positioning system (GPS) receiver, GLONASS receiver, and so forth. For indoor operation, the location sensor 114(5) may comprise an indoor position system, such as using Wi-Fi Positioning Systems (WPS). The location sensor 114(5) may provide information indicative of a relative location, such as "living room" or an absolute location such as particular coordinates indicative of latitude, longitude and altitude, or displacement with respect to a predefined origin.

The one or more sensors 114 may include one or more buttons 114(6) that are configured to accept input. The buttons 114(6) may comprise mechanical, capacitive, optical, or other mechanisms. For example, the buttons 114(6) may comprise mechanical switches that generate an input signal responsive to an applied force.

The sensors 114 may include one or more touch sensors 114(7). The touch sensors 114(7) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch. In some implementations the touch sensor 114(7) may be combined with the display device 106 to provide a touch sensitive display or touchscreen.

One or more microphones 114(8) acquire information about sound present in the environment. In some implementations, a plurality of microphones 114(8) may be used to form a microphone array. The microphone array may implement beamforming techniques to provide for directionality of gain.

A fingerprint sensor 114(9) acquires fingerprint data. The fingerprint sensor 114(9) may use an optical, ultrasonic, capacitive, resistive, or other detector to obtain an image or other representation of features of a fingerprint. For example, the fingerprint sensor 114(9) may comprise a capacitive sensor configured to generate an image of the fingerprint of the user 102. In other implementations, other input devices may be used to determine biometric data. For example, the image sensor 114(2) may be used to acquire an image of the iris of the user 102, which may then be used as biometric data to determine the user identifier.

One or more radio frequency (RF) receivers 114(10) may also be included as sensors 114. In some implementations, the RF receivers 114(10) may be part of transceiver assemblies. The RF receivers 114(10) may be configured to acquire RF signals associated with near-field communication (NFC), Wi-Fi, Bluetooth, ZigBee, Z-Wave, 4G, LTE, or other wireless data transmission technologies. The RF receivers 114(10) may provide information associated with data transmitted via radio frequencies, signal strength of RF signals, and so forth. For example, information from the RF receivers 114(10) may be used to facilitate determination of a location of the computing device 104, and so forth.

The display device 106 provides output that may be seen by the human eye. The output may be monochrome or color. The display device 106 may be emissive, reflective, or both. An emissive display device 106, such as using light emitting diodes (LEDs), emits light during operation. In comparison, a reflective display device 106, such as using an electrophoretic element, relies on ambient light for the image to be seen. Backlights or front lights may be used to illuminate reflective display devices 106 to provide visibility of the output in conditions where the ambient light levels are low.

The display mechanisms of display devices 106 may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 106 may operate as panels, projectors, and so forth.

The display devices 106 may be configured to present images. For example, the display devices 106 may comprise a pixel-addressable display. The image may comprise at least a two-dimensional array of pixels or a vector representation of an at least two-dimensional image.

In some implementations, the display device 106 may be configured to provide non-image data, such as text or numeric characters, colors, and so forth. For example, a segmented electrophoretic display device 106, segmented LED, and so forth, may be used to present information such as letters or numbers. The display devices 106 may also be configurable to vary the color of the segment, such as using multicolor LED segments.

The system 100 may include other output devices 132. Haptic output devices 214 are configured to provide a signal, which results in a tactile sensation to the user 102. The haptic output devices 214 may use one or more mechanisms such as electrical stimulation or mechanical displacement to provide the signal. For example, the haptic output devices 214 may be configured to generate a modulated electrical signal, which produces an apparent tactile sensation in one or more fingers of the user 102. In another example, the haptic output devices 214 may comprise piezoelectric or rotary motor devices configured to provide a vibration that may be felt by the user 102.

One or more audio output devices 216 are configured to provide acoustic output. The acoustic output includes one or more of infrasonic sound, audible sound, or ultrasonic sound. The audio output devices 216 may use one or more mechanisms to generate the acoustic output. These mechanisms may include, but are not limited to, the following: voice coils, piezoelectric elements, magnetorestrictive elements, electrostatic elements, and so forth. For example, a piezoelectric buzzer or a speaker may be used to provide acoustic output by an audio output device 216.

The other output devices 132 may also include actuators, scent dispensers, and so forth.

Figure 3:
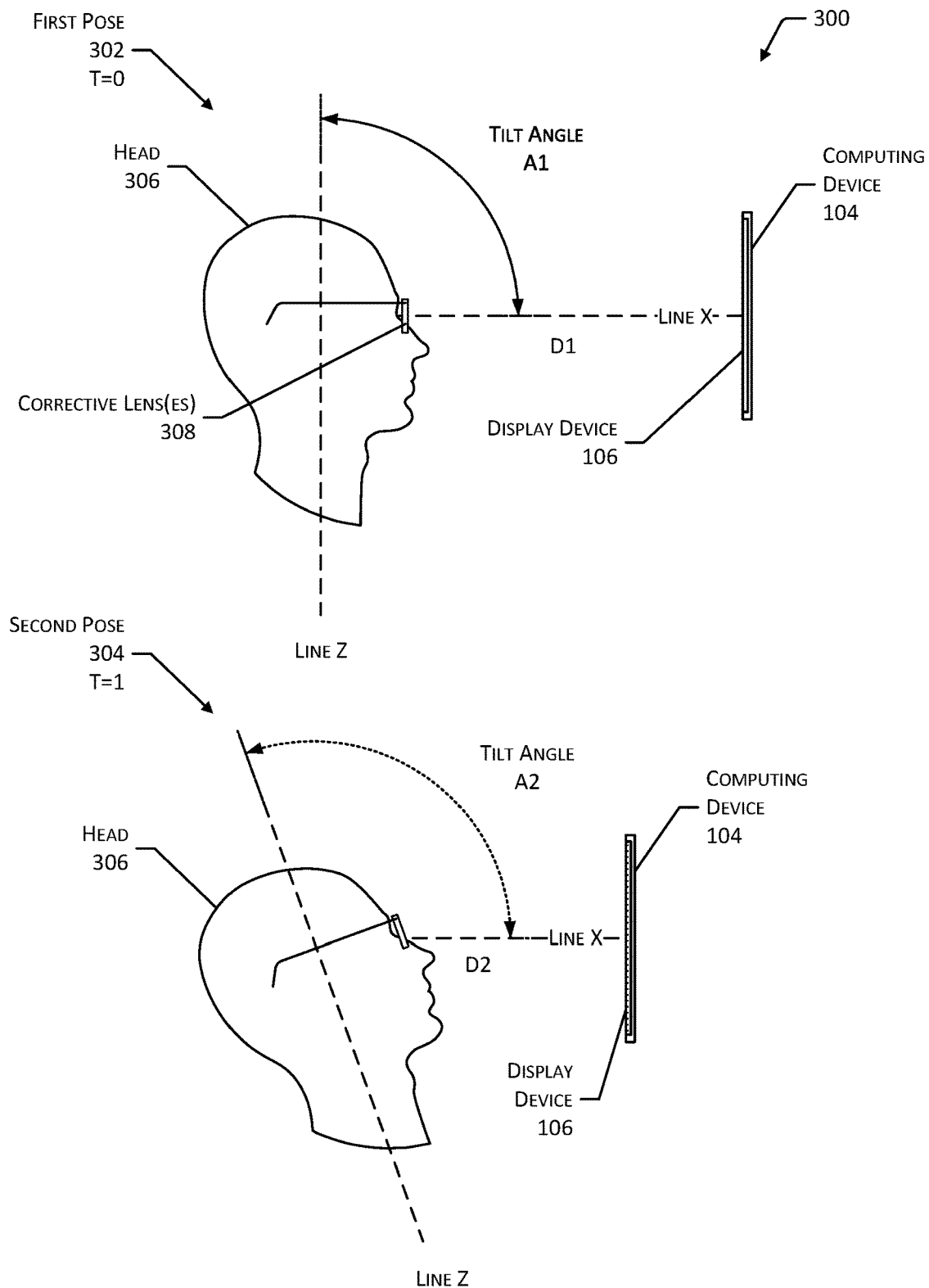
FIG. 3 illustrates tilt angles between the head of the user and the display device, according to one implementation.

FIG. 3 illustrates tilt angles between the head of the user 102 and the display device 106, according to one implementation. In this illustration a first pose 302 at time t=0 and a second pose 304 at time t=1 are shown.

In the first pose 302, a head 306 of the user 102 is oriented generally upright. A line Z is shown that may comprise a line formed by an intersection of the coronal plane and the sagittal plane of the head 306. A line X is also shown that may comprise a line that is orthogonal to a surface of the display device 106. In implementations where the display device 106 is curved, the line X may be orthogonal to a plane that is tangent to the display device 106 at a particular point.

In the first pose 302, the display device 106 is being held at a first distance D1. A first tilt angle A1 is described between the line Z and line X. For example, the first tilt angle A1 may be 90 degrees.

In the second pose 304, the display device 106 is being held at a second distance D2. A second tilt angle A2 is described between the line Z and line X. For example, the second tilt angle A2 may be 110 degrees. For example, the user 102 may have moved the display device 106 closer and tilted their head 306. In this illustration the user 102 is wearing corrective lenses 308, such as glasses. By changing the tilt angle of the user's head 306 relative to the display device 106, a different portion of the corrective lenses 308 are used to view the computing device 104.

During operation, the system 100 may acquire the input data 120 including distance data 120(1) and tilt angle data 120(2) at times t=0 and t=1.

Figure 4:
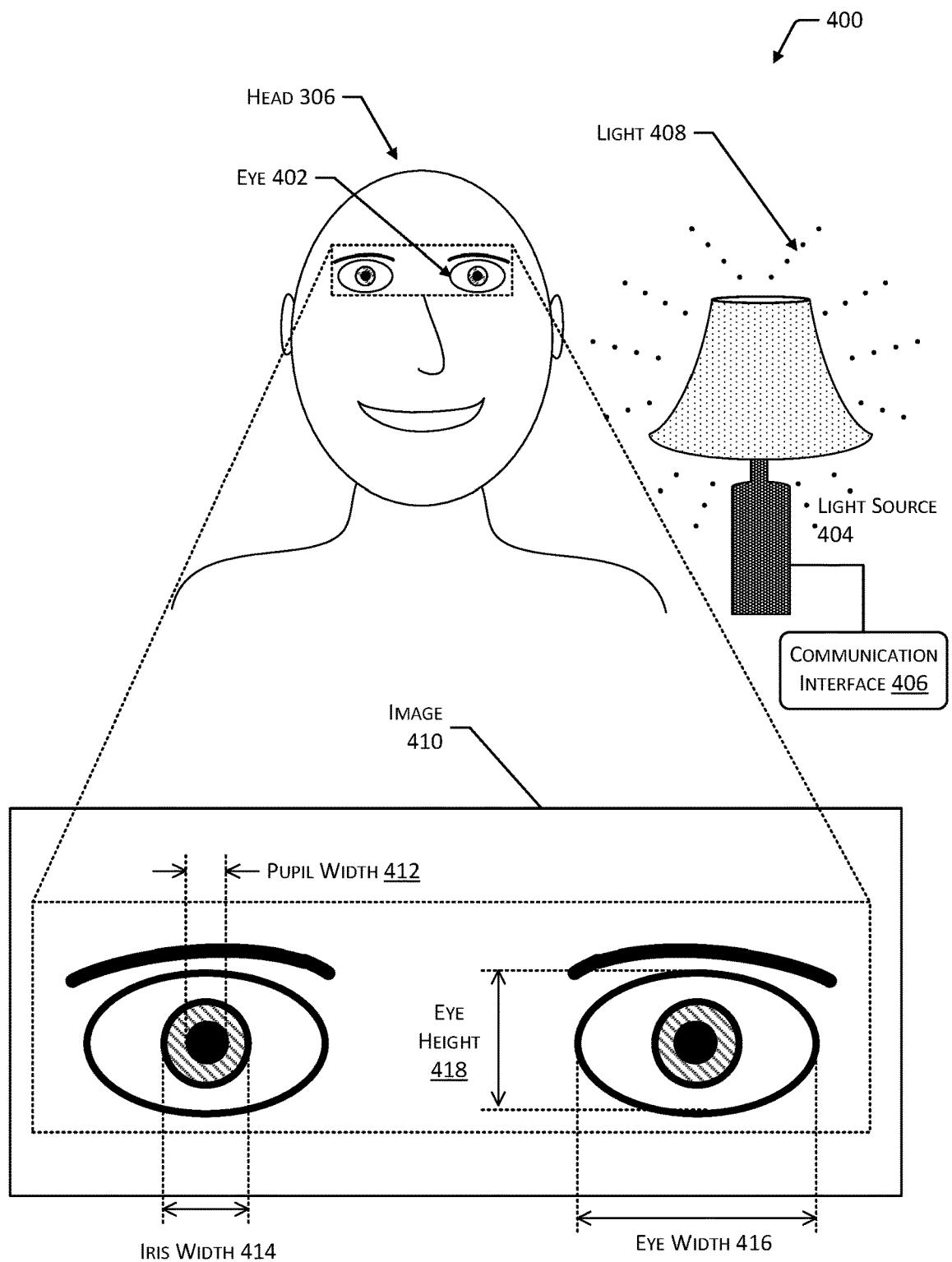
FIG. 4 depicts an image of the user's eyes and pupil width and control of a light source in the environment, according to one implementation.

FIG. 4 depicts an image of the user's eyes and pupil width and control of a light source in the environment, according to one implementation. The user 102 has eyes 402 on their head 306. A light source 404 in the ambient environment provides light 408 to the environment. The light source 404 may comprise a lamp, overhead light, and so forth. The light source 404 may have a communication interface 406. One or more commands may be sent to the light source 404 via the communication interface 406 to control operation of the light source 404. Commands may be sent to turn off the light 408, increase light output, decrease light output, and so forth. For example, the computing device 104 may send a command to set the light source 404 to a predetermined level of brightness. The light source 404 may also use the communication interface 406 to send data to other devices, such as the computing device 104. For example, the light source 404 may send data to the computing device 104 that indicates the light output or brightness of the light source 404.

As described above, the image sensor 114(2) may acquire an image 410 of the user 102 during operation of the system 100. The image 410 may include depictions of one or both eyes 402 of the user 102. The image 410 may be processed by one or more of the data processing modules 118 to determine a pupil width 412, an iris width 414, an eye width 416, an eye height 418, or other information. For example, an image classifier, neural network, or other techniques may be used to detect the pupils.

The pupil width 412 may be expressed in units including, but not limited to pixels, meters, or as a ratio relative to other features. In one implementation, the pupil width 412 may be determined as a ratio with respect to another feature in the image 410, such as a feature on the head 306 of the user 102. For example, the pupil width 412 may be calculated as an apparent diameter in pixels of the pupil divided by an apparent diameter in pixels of the iris width 414. In another example, the pupil width 412 may be a ratio of apparent diameter in pixels of the pupil divided by apparent diameter in pixels of the eye width 416. In other implementations other techniques may be used.

The depth of field of the eye 402 is the distance between the nearest and farthest objects that are acceptably focused. At any given time, depth of field of the user's 102 vision is affected by the size of the pupil. A constricted pupil has a smaller aperture than a dilated pupil. The smaller the aperture the greater the depth of field, and vice versa. The size of the pupil also affects the amount of light 408 that enters the eye 402. For example, in a dim room the pupil will dilate, presenting a relatively large aperture to allow more light 408 to enter the eye 402. This relatively large aperture decreases the depth of field of the user's vision.

These changes to depth of focus due to pupil size may change the distance D between the user 102 and the display device 106. For example, in daylight with the pupil constricted, the user 102 may have a greater depth of field and thus may maintain the display device 106 at a first distance D1. Continuing the example, in a dark room with the pupil dilated, the user 102 has a reduced depth of field and thus may maintain the display device 106 at a second distance D2 that differs from the first distance D1.

The input data 120 may include information about pupil width 412 at a given time. This information may be used to determine if the user 102 is experiencing a change in vision. For example, the pupil width 412 at a given time may be used in conjunction with the distance data 120(1) as inputs to a calculation to determine a visual acuity metric.

Information about the pupil width may also be used to determine if there is an unexpected response to stimuli. For example, if the pupil width 412 for both eyes 402 is greater than previously observed given a particular ambient light level, the advisory module 126 may generate recommendation data 128.

Information about the pupil width 412 may also be used to determine if there is an asymmetrical pupillary response between the left and right pupil widths 412 of the user 102 at a given time. For example, if the left pupil width 412 and the right pupil width 412 differ by greater than a threshold amount, the advisory module 126 may generate recommendation data 128.

The computing device 104 may change one or more of brightness of the display device 106 or light 408 from the light source 404 to elicit a particular pupillary response. For example, the computing device 104 may send a command for the light source 404 to increase to maximum brightness if the pupil width 412 of the user 102 exceeds a threshold value.

The eye height 418 is indicative of a distance between an upper lid margin and a lower lid margin of an eye 402. For example, a user 102 may have their eyes full open with a first eye height 418 or may squint to produce a second eye height 418 that is less than the first eye height 418. Continuing the example, the user data 120(5) may include the eye height 418 or information based on the eye height 418.

The eye height 418 may be expressed in units including, but not limited to pixels, meters, or as a ratio relative to other features. In one implementation, the eye height 418 may be determined as a ratio with respect to another feature in the image 410, such as a feature on the head 306 of the user 102. For example, the eye height 418 may be calculated as an apparent distance in pixels of a visible portion of the sclera divided by an apparent diameter in pixels of the eye width 416.

In some implementations, changes in eye height 418 or other techniques may be used to determine a blink rate, ratio of time the eye 402 is open, and so forth. This information may be used to determine the vision data 124. For example, if a user 102 is squinting as indicated by a decreased eye height 418, that may be indicative of impaired vision.

Figure 5:
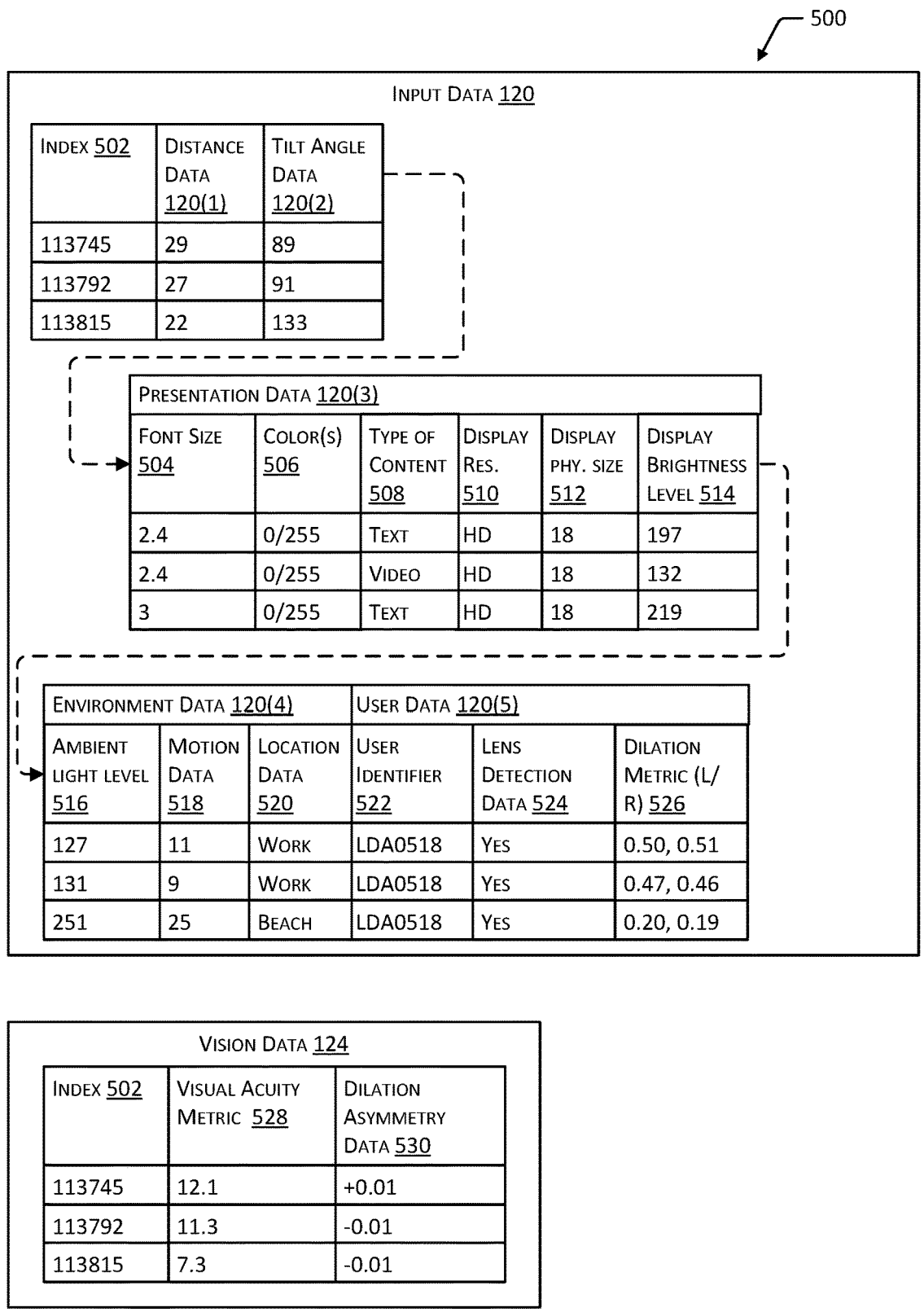
FIG. 5 depicts input data and vision data, according to one implementation.

FIG. 5 depicts input data 120 and vision data 124, according to one implementation. The input data 120 may include an index 502. For example, the index 502 may comprise a timestamp, sequence number, and so forth. The index 502 may be used to associate input data 120 with a particular time, window of time, event, session, and so forth.

The input data 120 may include the distance data 120(1) and the tilt angle data 120(2) as described above.

The presentation data 120(3) may include information about the presentation of information on the display device 106. The presentation data 120(3) may include one or more of font size 504, colors 506, type of content 508, font, and so forth. For example, the font size 504 may comprise a point size, pixel size on screen, actual size on the display device 106, and so forth. The colors 506 may include one or more of font color of text presented on the display device 106, background color for the text, and so forth. The type of content 508 may be indicative as to whether the predominate type of information being presented on the display device 106 is text, images, video, mixed media, and so forth. The user interface module 110 may provide at least a portion of the presentation data 120(3). For example, the user interface module 110 may provide information indicative of the font size 504 and the colors 506, and indicate that the information presented is text with some graphics.

The presentation data 120(3) may include information about the display device 106. For example, the presentation data 120(3) may include a display resolution 510, display physical size 512, and so forth. The display resolution 510 may provide information such as a particular format such as "HD" with a resolution of 1920×1080 pixels, while the display physical size 512 may indicate the physical dimensions of the display device 106. In other implementations the presentation data 120(3) may indicate the number of pixels per inch (PPI) for the display device 106. The presentation data 120(3) may be used to determine vision data 124 that is obtained from different devices. For example, by using the number of pixels per inch for the display device 106 and the font size 504, the vision data 124 may be generated that is associated with the user 102 reading text with a particular physical size as presented on the display device 106.

The presentation data 120(3) may include information about operation of the display device 106. For example, the presentation data 120(3) may include a display brightness level 514 that is indicative of the intensity of light 408 emitted by an emissive display. The display brightness level 514 may indicate the intensity of light 408 from a backlight of a liquid crystal display or intensity of light 408 emitted by an LED display. The presentation data 120(3) may include other information such as a contrast setting, color temperature, color correction values, and so forth. An operating system of the computing device 104 provide the presentation data 120(3) in some implementations.

The environment data 120(4) is indicative of the environment of the display device 106. The environment data 120(4) may include an ambient light level 516, motion data 518, location data 520, and other data. Changes in ambient light level 516 may affect vision. As described above, changing light levels may change dilation of the user's 102 pupils, changing the depth of field of their eyes 402. The ambient light sensor 114(3) that is proximate to the display device 106 may be used to acquire the ambient light level 516.

The motion data 518 may provide information about movement of the display device 106 or the computing device 104 (if they are separate). The motion data 518 may be used to determine the vision data 124. For example, as the user 102 reads text on the display device 106 while on a bumpy car ride, they may hold the display device 106 closer to their eyes 402 to mitigate the movement. The data analysis module 122 may disregard the distance data 120(1) obtained during this period if the motion data 518 is indicative of motion exceeding a threshold level. The motion data 518 may be determined based on sensor data from the IMU 114(4).

The location data 520 is indicative of one or more of absolute or relative location. For example, the location data 520 may comprise information about the geographic coordinates of the computing device 104. The location data 520 may be determined based on sensor data from the location sensor 114(5).

The input data 120 may include the user data 120(5). The user data 120(5) is associated with a particular user 102. The user data 120(5) may include a user identifier 522. The user identifier 522 is indicative of a particular user 102. The user identifier 522 may comprise an assigned value, login, a username, a real name, an identification code, and so forth. The user identifier 522 may be determined based on input from one or more sensors 114. For example, the user identifier 522 may be determined based on login information entered by the user 102 via the touch sensor 114(7), the microphone 114(8), keyboard, and so forth. In another example, the user identifier 522 may be determined based on biometric data obtained from an input device such as the fingerprint sensor 114(9), sound of the user's 102 voice as acquired by the microphone 114(8), and so forth. In yet another example, the user identifier 522 may be determined by performing facial recognition on an image 410 acquired by the image sensor 114(2) associated with the display device 106. Continuing the example, the image 410 of the user 102 obtained by the image sensor 114(2) mounted near the display device 106 may be processed by the facial recognition module 118(3) to identify the user 102 in the image 410 using one or more facial recognition techniques.

The user data 120(5) may include lens detection data 524 that is indicative of whether the user 102 is wearing lenses. For example, the user 102 may be wearing eyeglasses, contact lenses, have intraocular implants, and so forth. In one implementation, the lens detection data 524 may be based on output from the lens detection module 118(4) that determines if the image 410 of the user 102 appears to include eyeglasses. Other techniques may be used to generate the lens detection data 524. For example, the user 102 may manually enter that they wear glasses with multifocal lenses, have multifocal intraocular lens implants, wear single vision contact lenses, and so forth. In another example, the lens detection data 524 may be associated with a particular user identifier 522. Once the user identifier 522 has been determined, the associated previously stored lens detection data 524 may be associated with the corresponding input data 120.

The user data 120(5) may comprise a dilation metric 526 that is indicative of the pupil width 412 for one or both eyes 402. For example, the dilation metric 526 may comprise a ratio of the pupil width 412 to the iris width 414. In another example, the dilation metric 526 may comprise a ratio of the pupil width 412 to the eye width 416. In another implementation the dilation metric 526 may comprise the pupil width 412 expressed as a linear measurement, such as in millimeters.

The input data 120 may comprise sensor data that was acquired over a period and subsequently processed. The input data 120 associated with a particular index 502 may be based on sensor data obtained over a span of time extending from a first time to a second time. For example, the sensor data from the first time to the second time may be processed using various techniques including denoising, filtering, averaging, determining a minimum or maximum, linear regression analysis, and so forth to determine the input data 120 for a particular index 502.

At least a portion of the input data 120 is processed by the data analysis module 122 to determine vision data 124. The vision data 124 may be based on input data 120 from a particular time, or from a particular time interval. For example, a session may comprise the time spent while a user 102 is in front of the display device 106. The vision data 124 may be determined based on input data 120 obtained during the session. In another implementation the vision data 124 may be determined based on input data 120 associated with a plurality of sessions. For example, vision data 124 for the morning of a particular day may be based on input data 120 for the six sessions occurring between midnight and 12 pm.

The vision data 124 may include a visual acuity metric 528, dilation asymmetry data 530, or other data. The visual acuity metric 528 provides an indication of visual acuity of the user 102. In one implementation, the visual acuity metric 528 may be calculated as the distance data 120(1) in centimeters divided by the actual font size 504 as presented on the display device 106 in millimeters. For example, if the distance data 120(1) is 29 centimeters and the font size is 2.4 mm, the visual acuity metric 528 is 12.08. In another example, other input data 120 may be used to determine weighting factors such as a contrast difference between the colors 506.

The vision data 124 may include or be based on other input data. For example, the vision data 124 may comprise an average value of distance data 120(1) and tilt angle data 120(2) for a session or other interval indicated by an index 502 value.

The visual acuity metric 528 may be associated with particular index 502 values. For example, the visual acuity metric 528 for each session using input data 120 from that session. In another example, a visual acuity metric 528 may be based on input data 120 obtained across multiple sessions, such as a visual acuity metric 528 for the calendar day.

The vision data 124 may comprise information indicative of other aspects of the visual performance of the user 102. Visual performance may include measurements of aspects other than visual acuity. In one implementation, the vision data 124 may include other information, such as dilation asymmetry data 530. For example, the dilation asymmetry data 530 may comprise information that is indicative of a difference or percentage variance between the dilation metrics 526 for the left and right eyes 402.

The advisory module 126 uses the vision data 124 to determine recommendation data 128. For example, the vision data 124 in this illustration shows a decrease in the visual acuity metric 528 across three index 502 periods. The advisory module 126 may compare the vision data 124 to a previously determined threshold, analyzed using statistical analysis techniques to determine if a statistically significant change has taken place, and so forth. For example, the advisory module 126 may use a linear regression on the visual acuity metrics 528 to determine a trend line. The slope of the trend line in this example would be negative. If the slope exceeds a threshold value, recommendation data 128 may be generated.

In another example, the dilation asymmetry data 530 may be analyzed to determine if an asymmetry exceeding a threshold level is present. For example, if the dilation asymmetry data 530 exceeds a threshold value, recommendation data 128 may be generated.

Figure 6:
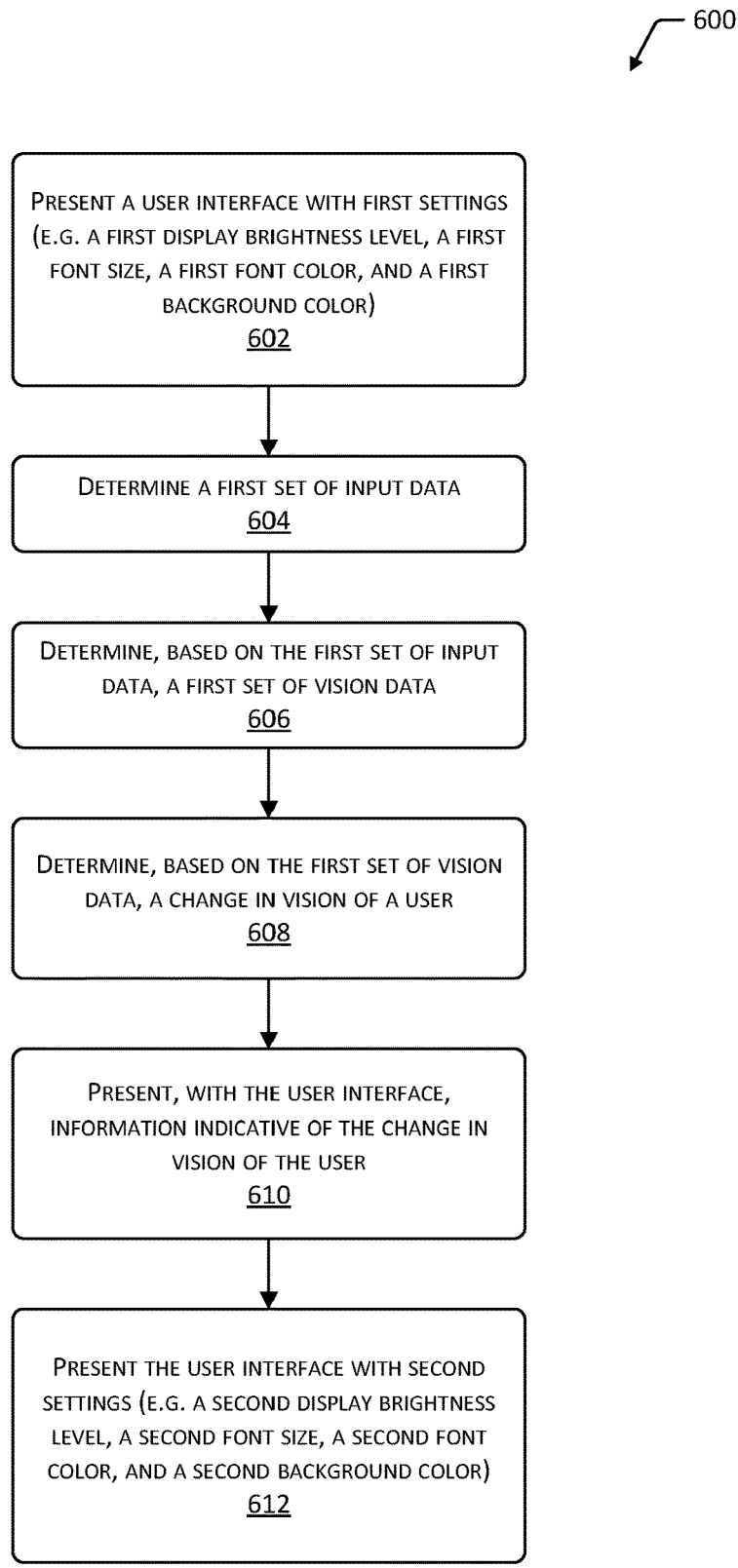
FIG. 6 illustrates a flow diagram of a process of determining a change in vision of a user, according to one implementation.

FIG. 6 illustrates a flow diagram 600 of a process of determining a change in vision of a user 102, according to one implementation. The process may be implemented at least in part by the computing device 104, a server, or other device.

At 602 a user interface is presented with first settings. For example, a visual user interface would be presented on the display device 106 with a first display brightness level 514, a first font size 504, a first font color, and a first background color.

In some implementations other characteristics of the visual user interface may be set. For example, one or more glyphs in a font may be modified to provide a "shadow" or "ghosting" effect to one side or another. Continuing the example, a shadow effect may be applied to a left side of a glyph or to a right side of a glyph. By providing different shadow effects and comparing to the data obtained, the system may be able to provide additional information on the user's 102 vision.

In another example, an audio user interface would be presented by the audio output device 216 at a first volume level.

In some implementations, the first settings may be previously defined and used during subsequent sessions or specifically to test the vision of the user. For example, use of the same settings during sessions on different days may improve the reliability of the input data 120 acquired and the subsequent vision data 124. In another example, the user 102 may initiate an assessment of their vision which would use predetermined settings to provide a uniform testing situation. In some situations, the predetermined settings may include settings the environment to a particular state. For example, a command may be sent for setting brightness of the light source 404 to a specified brightness level.

At 604 a first set of input data 120 is determined. For example, while the computing device 104 is in use during a session, the sensors 114 may acquire sensor data that is processed by the data processing modules 118 to determine the input data 120. The input data 120 may be obtained for a plurality of particular times. The input data 120 may include an index 502 such as a timestamp indicative of the particular time, distance data 120(1) indicative of a distance between a portion of the user's 102 head 306 and a display device 106 at the particular time, and tilt angle data 120(2) indicative of the tilt angle "A" between the user's 102 head 306 and the display device 106 at the particular time.

At 606 a first set of vision data 124 is determined based on the first set of input data 120. For example, the input data 120 obtained during the session may be processed by the data analysis module 122 to determine the first set of vision data 124. The vision data 124 includes information that is indicative of at least visual acuity of the user 102 over a period of time. For example, the vision data 124 may include visual acuity metrics 528 for different days.

At 608 a change in vision of the user 102 that exceeds a threshold is determined based on the first set of vision data 124. The change in vision may be determined with respect to the user's 102 specific history, a baseline value for a population of users 102, or other criteria. In one implementation, the first set of vision data 124 may be compared to previously stored vision data 124. For example, if the vision data 124 comprises a visual acuity metric 528 that is 20% less than the previously stored visual acuity metric 528 for that user 102, a change in vision may be determined. In another implementation, the first set of vision data 124 may be compared to one or more threshold values. For example, if the visual acuity metric 528 is below a threshold value, a change in vision relative to a baseline may be determined.

At 610 information indicative of the change in vision of the user 102 is presented in the user interface. For example, the advisory module 126 may process the vision data 124 and generate recommendation data 128. The recommendation data 128 may be presented in the user interface. For example, the recommendation data 128 may be presented as text in a visual user interface, as audio presented in an audio user interface, and so forth.

In some implementations the system 100 may attempt to mitigate the effects of changes. At 612, the user interface is presented using second settings that are based on one or more of the vision data 124 or the recommendation data 128. For example, the visual user interface would be presented on the display device 106 with a second display brightness level 514 that may be brighter than the first display brightness level 514, a second font size 504 that is larger than the first font size 504, a second font color and a second background color that have a greater contrast than the first font color and first background color, and so forth. In some situations, if color perception has been determined to be impaired, the second settings may include color choices for display elements that are perceptible to the user. For example, if the user 102 experiences deuteranopia, they may have difficulty discriminating between reds and greens. As a result, the second settings may avoid potentially imperceptible combinations, such as a green font on a red background. In another example, an audio user interface would be presented by the audio output device 216 at a second volume level that is greater than the first volume level.

Figure 7:
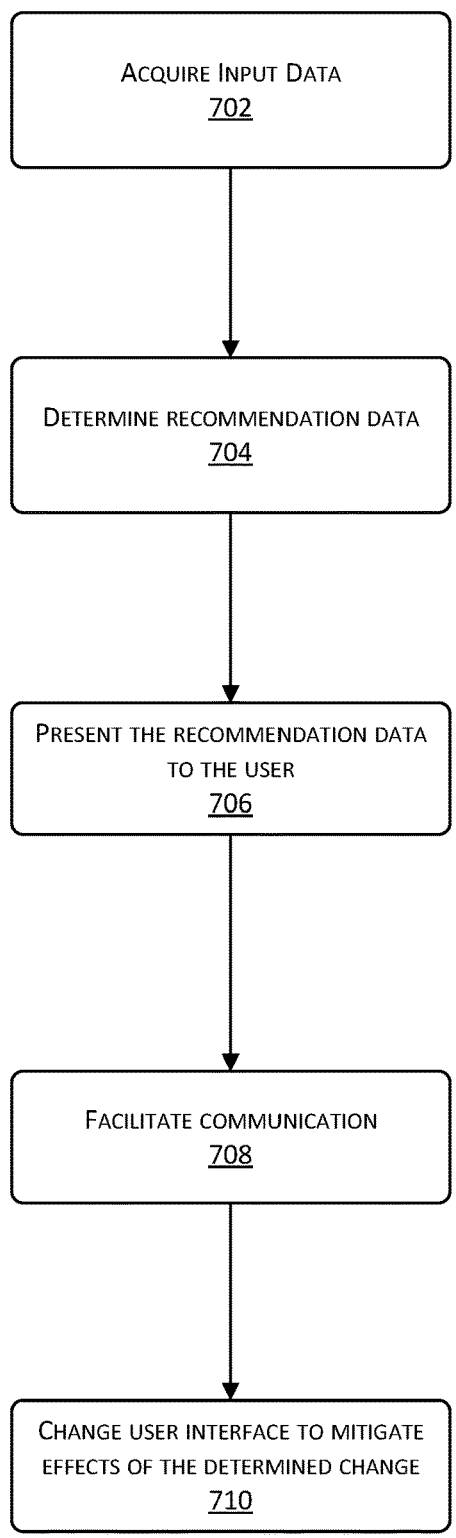
FIG. 7 illustrates a scenario in which input data is used to determine recommendation data, facilitate communication, and mitigate the effects of a vision change, according to one implementation.
Figure 7:
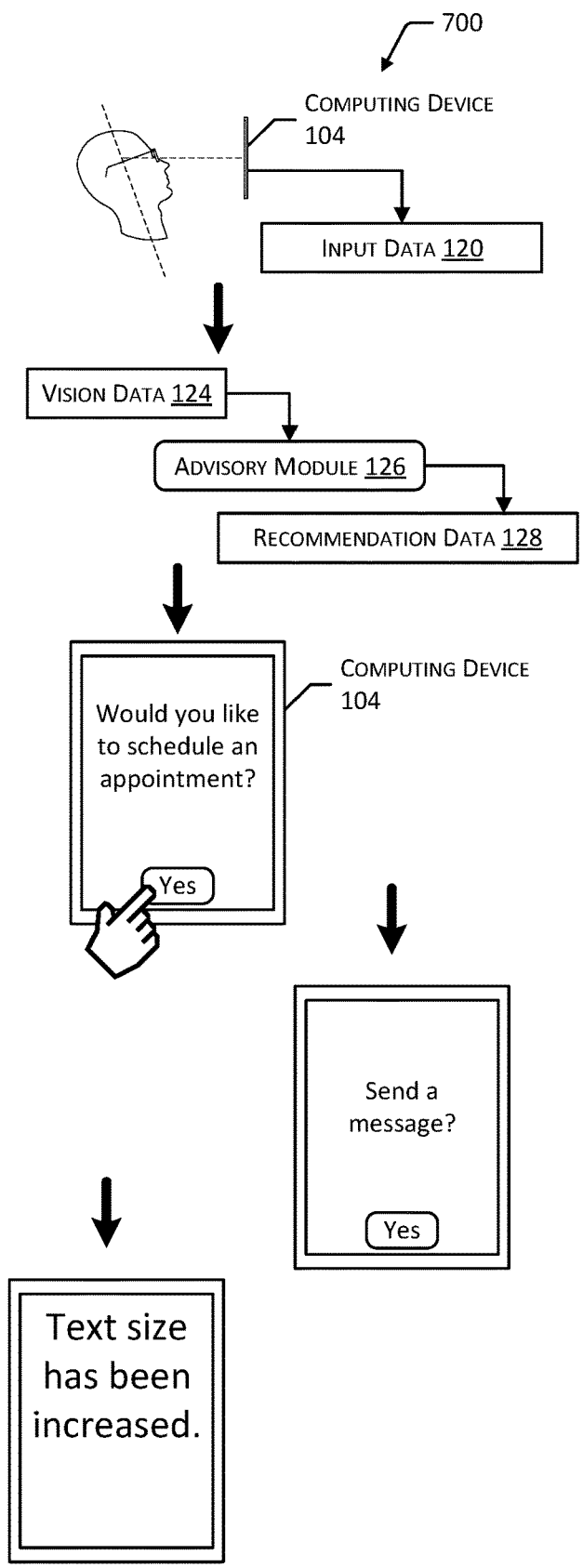

FIG. 7 illustrates a scenario 700 in which input data 120 is used to determine recommendation data 128, facilitate communication, and mitigate the effects of a vision change, according to one implementation. The scenario may be implemented at least in part by the computing device 104, a server, or other device.

At 702 input data 120 is acquired. For example, the user 102 may choose to opt in to use of the system, and sensor data from one or more of the sensors 114 may be acquired and processed by the data processing module(s) 118 to generate the input data 120.

At 704 recommendation data 128 is determined. For example, the vision data 124 is processed by the advisory module 126 to determine recommendation data 128.

At 706 the recommendation data 128 is presented to the user 102 or to an authorized party that is associated with the user identifier 522. For example, contact information for the authorized party may be associated with the user identifier 522. The recommendation data 128 may be used to generate a notification that is presented to the authorized party specified in the contact information. Continuing the example, the recommendation may be presented to the user 102, a parent, caregiver, health care provider, and so forth. For example, the user interface may present on the display device 106 a prompt asking the user 102 if they would like to schedule an appointment for an eye examination, if they have been having trouble reading, and so forth.

At 708 the system 100 facilitates communication between the user 102 or the authorized party and another party, such as a care provider. For example, the user 102 may activate a control associated with the prompt. Responsive to the activation, communication between the user 102 and the care provider may be facilitated. For example, a message may be sent to the care provider requesting an appointment, a calendar may be presented allowing the user 102 to self-schedule, a voice or video call with the care provider may be initiated, and so forth.

At 710 the user interface is changed to mitigate effects of the determined change. In this scenario a decrease in visual acuity was detected. As a result, the system 100 attempts to mitigate by increasing the font size 504 so the text presented on the display device is larger and easier to read. In other scenarios other mitigations may be taken as appropriate to the detected change. For example, if visual acuity improves, the size of the font may decrease.

The processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A method comprising:
    determining a first set of input data comprising, for a plurality of particular times:
        a timestamp indicative of the particular time,
        a distance between a portion of a head of a user and a display device at the particular time, wherein the distance is set by the user, and
        a tilt angle between the head and the display device at the particular time;
    determining, based on the first set of input data, a first set of vision data that is indicative of at least visual acuity of the user over a period of time;
    determining, based on the first set of vision data, a change in vision of the user that exceeds a threshold; and
    presenting, with a user interface, information indicative of the change in vision of the user.

2. The method of claim 1, the determining the first set of input data further comprising:
    determining a user identifier that is indicative of the user, wherein the user identifier is determined by one or more of:
        receiving login information from a first input device associated with the display device,
        receiving biometric data from a second input device associated with the display device, or
        performing facial recognition on an image acquired by an image sensor associated with the display device.

3. The method of claim 1, the determining the first set of input data further comprising:
    acquiring an image of at least a portion of the head at the particular time, and
    determining, using the image, that lenses are depicted on the head in the image.

4. The method of claim 1, the determining the first set of input data further comprising:
    acquiring an image of one or both eyes of the user at the particular time, and
    determining a dilation metric for the one or both eyes using the image, wherein the dilation metric is representative of pupil dilation.

5. The method of claim 1, further comprising:
    receiving distance data from a range camera that provides an image and corresponding distance measurements to a plurality of points within the image, wherein the distance data is associated with the particular time;
    determining a first portion of the head depicted in the image;
    determining a first distance associated with the first portion;
    determining a second portion of the head depicted in the image;
    determining a second distance associated with the second portion; and
    determining the tilt angle based on the first distance and the second distance.

6. The method of claim 1, the first set of input data further comprising one or more of:
    a resolution of the display device at the particular time,
    a physical size of the display device,
    a type of content presented on the display device at the particular time,
    a font size used to present text on the display device at the particular time,
    a display brightness level of the display device at the particular time, or
    a font color and a background color used to present text on the display device at the particular time.

7. The method of claim 1, the first set of input data further comprising one or more of:
    an ambient light level at the particular time as acquired by an ambient light sensor associated with the display device,
    accelerometer data at the particular time as acquired by an accelerometer associated with the display device,
    rotation data at the particular time as acquired by a gyroscope associated with the display device, or
    location data associated with the display device at the particular time.

8. The method of claim 1, further comprising:
    before acquiring input data for at least one of the plurality of particular times:
        setting a display brightness level of the display device; and presenting, at the particular time, a user interface with text comprising:
a first font size,
a first background color, and
a first font color.

9. The method of claim 1, further comprising:
responsive to the change in vision exceeding the threshold, performing one or more of:
setting a display brightness level of the display device,
setting a font size,
setting a first background color and a first font color, or
setting brightness of one or more light sources in an ambient environment that includes the display device.

10. The method of claim 1, further comprising:
determining a user identifier associated with the user;
determining contact information associated with the user identifier; and
sending a notification using the contact information.

11. The method of claim 1, further comprising:
determining a user identifier associated with the user;
determining contact information for a health care provider that is associated with the user identifier; and
presenting, with the user interface, a control that upon activation by the user initiates a communication with the health care provider.

12. A system comprising:
a memory storing computer-executable instructions; and
a hardware processor that executes the computer-executable instructions to:
determine first output that is presented on a display device at a first time;
determine a first distance from the display device to a head of a user at the first time;
determine second output that is presented on the display device at a second time;
determine a second distance from the display device to the head of the user at the second time;
determine a first difference between the first distance and the second distance;
determine the first difference exceeds a first threshold value;
determine, based on the first difference exceeding the first threshold value, recommendation data indicative of a change in visual acuity of the user; and
determine third output that is presented on the display device at a third time, wherein the third output is indicative of the recommendation data.

13. The system of claim 12, further comprising:
the hardware processor that executes the computer-executable instructions to:
determine a first image that is acquired at the first time;
determine, based on the first image, a first tilt angle between the display device and the head of the user;
determine a second image that is acquired at the second time;
determine, based on the second image, a second tilt angle between the display device and the head of the user;
determine a second difference between the first tilt angle and the second tilt angle;
determine the second difference exceeds a second threshold value; and
wherein the recommendation data is based on the second difference.

14. The system of claim 12, wherein:
the first output comprises text with a first font size, and the second output comprises text with the first font size; and
further comprising:
the hardware processor that executes the computer-executable instructions to:
determine fourth output that is presented on the display device at a fourth time with text having a second font size that is greater than the first font size.

15. A system comprising:
at least one memory storing computer-executable instructions; and
at least one hardware processor that executes the computer-executable instructions to:
determine a first set of input data comprising, for a plurality of particular times:
a timestamp indicative of a particular time,
a distance between a portion of a head of a user and a display device at the particular time,
determine, based on the first set of input data, a first set of vision data that is indicative of at least visual acuity of the user over a period of time;
determine, based on the first set of vision data, a change in vision of the user that exceeds a threshold; and
generate output indicative of the change in vision of the user.

16. The system of claim 15, wherein the distance is based on output from one or more of:
one or more image sensors,
an optical time of flight sensor,
a range camera, or
an ultrasound transducer.

17. The system of claim 15, the first set of input data further comprising one or more of:
a resolution of the display device at the particular time,
a physical size of the display device,
a type of content presented on the display device at the particular time,
a font size used to present text on the display device at the particular time,
a display brightness level of the display device at the particular time,
a background color and a font color used to present text on the display device at the particular time, or
an ambient light level at the particular time.

18. The system of claim 15, the first set of input data further comprising a user identifier that is indicative of the user, wherein the user identifier is determined by one or more of:
login information acquired by a first input device associated with the display device;
biometric data acquired by a second input device associated with the display device, or
facial recognition of an image acquired by an image sensor associated with the display device.

19. The system of claim 15, further comprising:
an image sensor; and
the at least one hardware processor executes the computer-executable instructions to:
acquire, using the image sensor, image data of at least a portion of the head at the particular time;
determine, using the image data, whether lenses are present on the head; and
wherein the first set of input data further comprises whether lenses are present on the user's head at the particular time.

20. The system of claim 15, further comprising:
an image sensor; and the at least one hardware processor executes the computer-executable instructions to:
  acquire image data, using the image sensor, of one or both eyes of the user at the particular time;
  determine, using the image data, a dilation metric for the one or both eyes using the image data, wherein the dilation metric is representative of pupil dilation; and
  wherein the first set of input data further comprises the dilation metric.

\* \* \* \* \*